United States Patent
Blum et al.

(10) Patent No.: US 6,399,813 B1
(45) Date of Patent: Jun. 4, 2002

(54) PROCESS FOR THE PREPARATION OF FLUID BED VINYL ACETATE CATALYST

(75) Inventors: Patricia Rae Blum, Macedonia; Larry Michael Cirjak, Burton; Marc Anthony Pepera, Northfield; Christos Paparizos, Willowick; George Frederick Salem, Cleveland Heights; Michael James Baker, Shaker Heights, all of OH (US)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 09/929,256

(22) Filed: Aug. 14, 2001

Related U.S. Application Data

(60) Division of application No. 09/343,832, filed on Jun. 30, 1999, which is a continuation of application No. 08/720,496, filed on Sep. 30, 1996, now abandoned, which is a continuation-in-part of application No. 08/376,180, filed on Jan. 20, 1995, now Pat. No. 5,591,688, which is a continuation-in-part of application No. 08/200,130, filed on Feb. 22, 1994, now Pat. No. 5,466,652.

(51) Int. Cl.$^7$ .............................................. C07C 67/055
(52) U.S. Cl. ..................................... 560/245; 5022/326
(58) Field of Search ......................... 560/245; 502/326

(56) References Cited

U.S. PATENT DOCUMENTS

| | | | |
|---|---|---|---|
| 3,117,990 A | 1/1964 | Adachi et al. | 266/498 |
| 3,275,680 A | 9/1966 | Holzrichter et al. | 260/497 |
| 3,642,659 A | 2/1972 | Dorn et al. | 252/435 |
| 3,670,014 A | 6/1972 | Fernholz et al. | 260/497 A |
| 3,686,287 A | 8/1972 | Knights | 260/497 A |
| 3,687,993 A | 8/1972 | Hornig et al. | 260/430 |
| 3,743,607 A | 7/1973 | Sennewald et al. | 252/430 |
| 3,759,839 A | 9/1973 | Fernholz et al. | 252/431 C |
| 3,761,513 A | 9/1973 | Seenewald et al. | 260/497 A |
| 3,775,342 A | 11/1973 | Kronig et al. | 252/430 |
| 3,822,308 A | 7/1974 | Kronig et al. | 260/49 A |
| 3,867,308 A | 2/1975 | Elliott, Jr. | 252/455 Z |
| 3,939,199 A | 2/1976 | Fernholz et al. | 260/469 |
| 3,950,400 A | 4/1976 | Fernholz et al. | 260/497 A |
| 4,048,096 A | 9/1977 | Bissot | 252/430 |
| 4,087,622 A | 5/1978 | Nakamura et al. | 560/245 |
| 4,188,490 A | 2/1980 | Hinnenkamp et al. | 560/245 |
| 4,280,929 A | 7/1981 | Shaw et al. | 252/439 |
| 4,326,993 A | 4/1982 | Chester et al. | 252/455 Z |
| 4,349,462 A | 9/1982 | Velenyi et al. | 252/455 R |
| 4,377,500 A | 3/1983 | Grasselli et al. | 252/432 |
| 4,392,987 A | 7/1983 | Laine et al. | 252/448 |
| 4,407,734 A | 10/1983 | Denton et al. | 502/9 |
| 4,442,223 A | 4/1984 | Chester et al. | 502/68 |
| 4,463,200 A | 7/1984 | Beard, Jr. et al. | 570/224 |
| 4,517,377 A | 5/1985 | Isshiki et al. | 560/261 |
| 4,631,264 A | 12/1986 | Hagen | 502/243 |
| 4,710,484 A | 12/1987 | Dolhyj et al. | 502/208 |
| 4,764,498 A | 8/1988 | Wissner et al. | 502/251 |
| 4,808,559 A | 2/1989 | Sommer et al. | 502/63 |
| 4,810,369 A | 3/1989 | Scherzer | 208/120 |
| 4,845,070 A | 7/1989 | Montag | 502/243 |
| 4,933,204 A | 6/1990 | Warren, Jr. et al. | 427/53.1 |
| 4,978,778 A | 12/1990 | Isshiki et al. | 560/261 |
| 5,051,394 A | 9/1991 | Haruta et al. | 560/324 |
| 5,179,056 A | 1/1993 | Bartley | 502/170 |
| 5,179,057 A | 1/1993 | Bartley | 502/170 |
| 5,185,308 A | 2/1993 | Bartley et al. | 502/170 |
| 5,189,004 A | 2/1993 | Bartley | 502/170 |
| 5,225,388 A | 7/1993 | Wunder et al. | 502/170 |
| 5,314,858 A | 5/1994 | Colling | 502/330 |
| 5,352,645 A | 10/1994 | Schwartz | 502/262 |
| 5,432,141 A | 7/1995 | Bradzil et al. | 502/311 |
| 5,466,652 A | 11/1995 | Paparizos et al. | 502/330 |
| 5,576,457 A | 11/1996 | Abel | 560/245 |
| 5,998,329 A | 12/1999 | Derolf et al. | 502/407 |

FOREIGN PATENT DOCUMENTS

| | | |
|---|---|---|
| CA | 2018991 | 12/1990 |
| EP | 0672453 | 9/1995 |
| GB | 1103125 | 2/1968 |
| GB | 1257043 | 12/1971 |
| GB | 1266623 | 3/1972 |
| GB | 1266624 | 3/1972 |
| GB | 1283737 | 8/1972 |
| GB | 2003878 | 3/1979 |
| JP | 62079841 | 4/1987 |
| JP | 01148342 | 6/1989 |
| JP | 03245844 | 11/1991 |
| JP | 07196310 | 8/1995 |
| RU | 2060937 | 5/1996 |
| ZA | 68/7990 | 12/1968 |

OTHER PUBLICATIONS

Kawaguchi, et al., "Method of an Activated Carbon Supported Zinc Acetate Catalyst," Applied Catalysis, 32, pp. 23–36 (1987).

Kawaguchi, et al., "Activity and Deactivation of a Catalyst for Vinyl Acetate Synthesis in an Industrial Fluidized Reactor," Applied Catalysis, 36, pp. 67–79 (1988).

Kawaguchi, et al., "Continuous Preparation of Activated Carbon Supported Zinc Acetate Catalyst and Industrial Synthesis of Vinyl Acetate from Acetylene," 42, pp. 113–127 (1988).

*Primary Examiner*—Bekir L. Yildirim
(74) *Attorney, Agent, or Firm*—Wallace L. Oliver

(57) ABSTRACT

A process for the preparation of a fluid bed vinyl acetate (VAM) catalyst comprising impregnating a support comprising a mixture of substantially inert microspheroidal particles with a solution comprising a metal salt of Pd and M, wherein M comprises Ba, Cd, Au, La, Nb, Ce, Zn, Pb, Ca, Sr, Sb or mixtures thereof, reducing the metal salts to form a deposit of Pd and M on the support surface and impregnating the support with at least one alkali metal salt. At least 50% of the particles used for the microspheroidal support have a particle size below 105 microns.

27 Claims, No Drawings

PROCESS FOR THE PREPARATION OF FLUID BED VINYL ACETATE CATALYST

This application is a division of U.S. application Ser. No. 09/343,832 filed Jun. 30, 1999, which is continuation of U.S. application Ser. No. 08/720,496 filed Sep. 30, 1996, abandoned, which is a continuation-in-part of U.S. application Ser. No. 08/376,180, filed Jan. 20, 1995, now U.S. Pat. No. 5,591,688, which is a continuation-in-part of U.S. application Ser. No. 08/200,130, filed Feb. 22, 1994, now U.S. Pat. No. 5,466,652, incorporated by reference herein.

BACKGROUND OF THE INVENTION

Field of the Invention

The present invention relates to a process for producing a fluid bed palladium-promoted catalyst useful in the production of vinyl acetate from ethylene, acetic acid and oxygen-containing gas. In addition, the present invention relates to a novel fluid bed support and process of using the support for the manufacture of palladium-promoted fluid bed catalyst used in the manufacture of vinyl acetate.

The production of vinyl acetate by reacting ethylene, acetic acid and oxygen together in the gas phase in the presence of a catalyst is known. Typically, the catalysts are in fixed bed form and supported on a porous carrier material such as silica or alumina.

Early examples of these catalysts show that palladium and gold are distributed more or less uniformly throughout the carrier (see, for example, U.S. Pat. Nos. 3,275,680, 3,743,607 and 3,950,400 and Great Britain Patent No. 1,333,449 and South African Patent No. 687,990). Subsequently, it was recognized that this was a disadvantage since it was found that the material on the inner part of the carrier did not contribute to the reaction since the reactants did not significantly diffuse into the carrier. To overcome this problem, new methods of catalyst manufacture were devised with the aim of producing catalyst in which the active components were concentrated on the outer-most shell of the support. For example, Great Britain Patent No. 1,500,167 claims catalyst in which at least ninety percent of the palladium and gold is distributed in that part of the carrier particle which is not more than thirty percent of the particle radius from the surface. In addition, Great Britain Patent No. 1,283,737 teaches that the degree of penetration into the porous carrier can be controlled by pre-treating the porous carrier with an alkaline solution of, for example, sodium carbonate or sodium hydroxide. Another approach which has been found to produce particularly active catalyst is described in U.S. Pat. No. 4,048,096 and other methods of producing shell-impregnated catalyst are disclosed in U.S. Pat. Nos. 4,087,622 and 5,185,308. Each of these patents is primarily concerned with the manufacture of fixed bed catalyst useful for the manufacture of vinyl acetate. However, U.S. Pat. No. 3,950,400 also discloses that the catalyst disclosed therein may be used in a fluid bed reactor. In addition, Great Britain Patent No. 1,266,623 allegedly discloses a fluid bed catalyst for vinyl acetate manufacture which comprises palladium promoted with various alkali, alkaline earth or other metals.

It would be economically beneficial if the manufacture of vinyl acetate could be performed in a fluid bed process as well as a fixed bed process. Some of the typical benefits from a fluid bed process would be that the fluid bed reactor design is simpler than a multi-tubular fixed bed reactor, increased catalyst life is to be expected because no deactivation would take place due to hot spots which are typical of a fixed bed reactor, continuous addition of make-up catalyst can maintain peak performance and virtually eliminate catalyst change-outs, and higher production rates can be expected because substantially higher oxygen levels may be safely fed into the reactor without producing a flammable mixture.

Until the discovery of the process of the present invention, the preparation of palladium-promoted catalyst in fluid bed form has not led to catalyst having the necessary properties leading to a viable economical fluid bed process for the manufacture of vinyl acetate. The process of the present invention overcomes the problems associated with the prior art resulting in a catalyst giving high performance and adequate attrition resistance so that it may be used in the manufacture of vinyl acetate.

SUMMARY OF THE INVENTION

It is the primary object of the present invention to provide a process for the manufacture of a fluid bed palladium-metal-promoted alkali metal catalyst useful in the manufacture of vinyl acetate.

It is another object of the present invention to provide a novel support for use in the production of a fluid bed palladium-metal-alkali-metal-promoted catalyst useful in the fluid bed manufacture of vinyl acetate.

It is still another object of the present invention to provide a novel process for the production of a support useful in the manufacture of vinyl acetate catalyst.

Additional objects and advantages of the invention will be set forth in part in the description which follows and, in part, will be obvious from the description or may be learned by practice of the invention. The objects and advantages of the invention may be realized and attained by means of the instrumentalities and combinations particularly pointed out in the appended claims.

To achieve the foregoing objects of the present invention, the process of manufacturing a fluid bed vinyl acetate catalyst characterized by the following formula comprising Pd—M—A wherein M equals barium, cadmium, gold, lanthanum, niobium, cerium, zinc, lead, calcium, strontium, antimony, or mixtures thereof; and A equals at least one alkali metal or mixture thereof comprises impregnating a pre-formed microspheroidal support wherein at least 50% of the particles have a particle size diameter selected to be below 105 microns with a solution comprising a metal salt of the palladium, M and at least one alkali metal and drying the impregnated catalyst. The substantially inert particulate support typically comprises microspheroidal particles selected from the group consisting of alumina, silica, titania, zirconia, and/or mixtures thereof.

In another embodiment of the present invention the process is performed using an aqueous solution free or substantially free of any organic solvent.

In a preferred embodiment of the present invention the metal salt of the alkali metal is separately impregnated onto the support, preferably subsequent to the impregnation of the solution comprising the salts of palladium and M element onto the support material.

In another embodiment of the present invention, the impregnated support may be subjected to known reduction procedures (e.g., heating under reducing conditions) to form a deposit of palladium and M on the surface of the support. The reduction can take place either before or after the deposition of the alkali metal solution.

In a still further preferred embodiment of the present invention the catalyst is dried at a temperature below 80° C, preferably between about 60° to 70° C.

In another preferred embodiment of the present invention the particle size(particle diameter) of the substantially inert support material is selected such that at least 50% of the particles are below about 105 microns. Preferably, at least 75% of the particles are below 105 microns, especially preferred being at least 85% below 105 microns. Finally the preferred support is substantially free of sodium.

In another embodiment of the present invention, the support for the manufacture of the vinyl acetate catalyst comprises a mixture of substantially inert microspheroidal particles having a pore volume of between 0.2 to 0.7 cc/g and/or a surface area of between 50 to 200 m²/g and at least 50% of said particle are less than 105 microns.

In a preferred aspect of this embodiment of the present invention, at least 75% of the particles are below 105 microns, especially preferred being at least 85% below 105 microns. 76

In another embodiment of the present invention, the support for the manufacture of the vinyl acetate catalyst comprises microspheroidal inert particles, preferably silica, zirconia, alumina, titania or mixtures thereof wherein said particles have a pore volume of between 0.2 to 0.7 cc/g and/or a surface area of between 50 to 200 m²/g and are obtained from a mixture of less than 100% to 20% inert support sol and greater than zero percent to 80% dried inert particles.

In a preferred embodiment of this aspect of the present invention, the pore volume of the inert particles is between 0.3 to 0.65 cc/g, especially preferred being 0.4 cc to 0.55 cc/g.

In a further preferred embodiment of this aspect of the present invention, the surface area is between 50 to 150 m²/g, especially preferred being 60 to 125 m²/g.

In a further aspect of this embodiment of the present invention, the silica microspheroidal support material is manufactured by mixing between 20% to less than 100% silica sol with 80% to greater than zero percent silica such as Aerosil®, spray drying said mixture at an elevated temperature of between 115° to 280° C., preferably 130° to 240° C., and calcining said spray dried particles preferably at a temperature of between 550° to 700° C., preferably between 630° to 660° to form the support material.

Typically, the weight percent of the palladium, M and alkaline in the catalyst of the present invention are: 0.1 to 5.0 wt % palladium, preferably 0.2 to 4.0 wt %; greater than 0 to 10 wt % alkali metal, preferably 0.1 to 8.0 wt %, most preferably 0.1 to 5.0 wt %; greater than 0 to about 5.0 wt % M, preferably 0.1 to about 4.0 wt %.

The catalysts of the present invention may be used in a fluid bed reactor for the reaction of ethylene with oxygen to produce vinyl acetate. The reaction temperature is suitably 100° to 250° C., preferably 135° to 190° C. The reaction pressure is suitably 50 to 200 psig, preferably 75 to 150 psig.

DETAILED DESCRIPTION OF THE INVENTION

Reference will now be made in detail to the present preferred embodiment of the invention of which the following examples are set forth for illustrative purposes only.

REACTOR TESTING FOR EXAMPLES 1 TO 20

The catalysts were tested in a bench scale fluid bed reactor with a maximum catalyst capacity of 40 cc. Thirty cc of catalyst or catalyst-plus-diluent was the typical volume of solid loaded into the reactor. In general, sufficient catalyst was used such that the reactor contained 0.093 g of palladium metal with each catalyst evaluation. A total of 30 cc volume was obtained by mixing sufficient inert microspheroidal silica with the active catalyst prior to reactor testing. The reactor was equipped with two feed inlets. For some of the experiments of this study, ethylene, acetic acid, and oxygen all entered the reactor through the lower inlet and nitrogen only was fed through the central inlet. In other tests, additional oxygen was fed through the central feed inlet. This central inlet was located 2.5" above the lower feed inlet.

The reactor pressure was controlled at 115 psig and all lines leading to and from the reactor were heat traced and maintained at 150° to 155° C. order to prevent condensation of liquid feeds or products. Typical temperatures for the ago fluid bed reactor can vary from 100° to 250° C., preferably 135° to 190° C.

The gaseous reactor effluent was analyzed on-line using a Hewlett Packard Model 5890 gas chromatograph equipped with both TCD and FID detectors. Oxygen, nitrogen, ethylene and carbon dioxide were separated on a 13× mole sieve column parallel with 10% carbowax 20M on 80/100 Chromosorb WAW and 23% SP2700 on 80/100 Chromosorb PAW, and quantitated with the TCD. Vinyl acetate and acetic acid were separated on a 4% carbowax 20M on 80/120 carbopack column and quantitated with the FID.

Support Preparation

Two types of preformed microspheroidal silica were prepared and utilized as supports in the practice of the present invention. Prior to use, all supports were sieved and a specific particle size distribution of the support was used in all catalyst preparations:

5% of the particles are less than 105 microns but greater than 88 microns

70% of the particles are less than 88 microns but greater than 44 microns

25% of the particles are less than 44 microns

It should be understood the particle size distribution recited above is not intended to be limiting and that variations in this distribution are contemplated depending upon reactor size and operating conditions.

Support 1

Support 1 was prepared by spray drying a mixture of Nalco (Nalco Chemical Company) silica sol 1060 and DeGussa Aerosil® (DeGussa Chemical Company) silica. In the dried support, 80% of the silica came from the sol and 20% of the silica came from the Aerosil®. The spray dried microspheres were calcined in air at 640° C. for 4 hours.

Aerosil® silica is the trade name of Degussa's fumed silica. This material has high surface area (~200 m²/g), essentially no micropores, uniform particle size distribution in the nm-range (1×10⁻⁹ meter), and is free of sodium. Fumed silica having properties comparable to Aerosil® may be produced by other companies and may be used in the place of Aerosil® in the preparation of Support 1.

Nalco silica sol 1060 is particularly advantageous for use in our application because of large mean particle size of the silica particles in the sol, 60 millimicrons. These larger silica particles pack less efficiently than smaller sol particles (~30 millimicrons as in Nalco 2327) and yield a final support higher in pore volume in the mesopore region and lower in micropore volume. Other silica sols which have a similarly large (~40 to 80 millimicrons) mean particle size of the silica may be utilized in the place of the 1060 silica sol in the preparation of Support 1.

Support 2

A series of microspheroidal supports (Supports 2A–2D) containing KA-160 (Sud Chemie) were prepared as follows:
Support 2A: 75% $SiO_2$ from KA-160 with 25% $SiO_2$ from Sol 750 g of KA-160 was ground to pass through a 35 mesh screen and washed to remove any soluble impurities, such as chloride ions. This solid silica was then mixed with 694.4 g of Snotex-N-30 (Nissan Chemical) (36 wt % solids) silica sol and 556 g distilled water. This mixture was milled overnight in a jar mill. The smooth slurry was then spray dried to form microspheroidal particles suitable for use in a fluid bed reactor. The microspheroidal support was then calcined at 640° C. in air for 4 hours.

The role of the KA-160 support is to provide much of the pore structure within the microspheroidal particle. The fixed bed support, KA-160, is produced by Sud Chemie and has properties which are advantageous for use in vinyl acetate catalyst preparation. Moderate surface area (160 $m^2/g$), little or no microporosity, and substantial porosity (~0.57 cc/g) in the mesopore region are advantageous properties of KA-160. Alternative fixed bed catalyst supports are available with surface area and pore volume properties similar to KA-160 (little or no micropores, mesopore volume of ~1.5–0.25 cc/g, and surface area 80–200 $m^2/g$). These supports may be utilized in the place of KA-160 in the preparation of Support 2.

Support 2B: 65% $SiO_2$ from KA-160 with 35% $SiO_2$ from Sol

This support was prepared in the same manner as Support 2A except that 227.5 g of KA-160, 408.3 g of Snotex-N-30 (30 wt % solids) and 64 g of distilled water were used.

Support 2C: 50% $SiO_2$ from KA-160 with 50% $SiO_2$ from Sol

This support was prepared in the same manner as Support 2A except that 175 g of KA-160 and 583.3 g of Snotex-N-30 (30 wt % solids) were used.

Support 2D: 75% $SiO_2$ from KA-160 with 25% $SiO_2$ from Sol

This support was prepared in the same manner as Support 2A except that 262 g of KA-160, 219 g of Nalco 2327 (40 wt % solids) (Nalco Chemicals Company) and 219 g of distilled water were used.

Each type of microspheroidal silicas prepared above may be used advantageously in the preparation of fluid bed vinyl a acetate monomer catalyst according to the process of the present invention. For use in the manufacture of fluid bed catalysts via impregnation with active metals, these supports provided unexpected superior physical properties for the vinyl acetate catalysts of the present invention compared to any readily available supports. Selected analytical data on all supports are included in Table 1 below.

TABLE 1

PHYSICAL PROPERTIES OF CUSTOMIZED MICROSPHEROIDAL SILICA SUPPORTS

| Support | Wt % Solids in Slurry | Pore Vol r ≤ 4,500 A (cc/g) | Tot Pore Vol (cc/g) | Ap Bulk Density (g/cc) | SA $m^2/g$ | Calcin Time/ Temp | Attrition Resist Loss 0–20 hrs |
|---|---|---|---|---|---|---|---|
| Support 1 | 62 | 0.39 | 0.46 | 0.78 | 124.4 | 4 hr/ 640° C. | <5% |
| Support 2A | 50 | 0.60 | 0.60 | 0.65 | 175.5 | 4 hr/ 640° C. | 0.33% |
| Support 2B | 50 | 0.39 | 0.39 | 0.72 | 184.4 | 4 hr/ 640° C. | 0.35% |
| Support 2C | 46 | 0.27 | 0.33 | 0.77 | 191.9 | 4 hr/ 640° C. | 1.65% |
| Support 2D | 50 | 0.62 | 0.63 | 0.60 | 156.0 | 4 hr/ 640° C. | |

Catalyst Preparation

The general method utilized in the preparation is summarized below.

Typically, the microspheroidal support is impregnated with a solution (or solutions) of the active metals using the incipient wetness technique. Compounds of the active metals, palladium, M element (e.g. gold) and potassium acetate, may be dissolved in the appropriate ratios in a suitable solvent, then impregnated upon the microspheroidal support. In general, it is desirable if all of the active metals to be used in a catalyst preparation are dissolved in a single portion of solvent which is of the volume just adequate to fill the pore volume of the support. In some instances a desired promoter may not be soluble in the same solvent as the other metal compounds to be used. In this case a solution containing some of the metal components may be impregnated upon the support, followed by impregnating a second solution containing the remaining components. Solvents which are useful include water and volatile organic solvents such as: carboxylic acids with four carbons or less, alcohols, ethers, esters, and aromatics. After the wet catalyst is dried, it may be used for the production of vinyl acetate or it may first be reduced by means known to those skilled in the art.

In general, when acetic acid is present and the catalyst is heated at an elevated temperature (~100° C.) the catalyst darkens to black and becomes inactive. Additionally, when a solution of palladium acetate (with or without other metal acetates) is heated to too high a temperature or for too long, the solution changes color from the original red-orange to a greenish color and a black precipitate forms. In general, 60° C. is a safe temperature to work at, but up to ~80° C. has been used for brief periods of time, to dissolve the palladium acetate.

EXAMPLE 1

A catalyst having the following composition 0.75 wt % Pd, 0.32 wt % Au and 2.88 wt % K was prepared by dissolving palladium acetate in an acetic acid solution of the gold acetate reagent described in U.S. Pat. No. 4,933,204 and impregnating this combined solution upon a preformed microspheroidal Support 2A identified above. The solid was dried at 60° C. using a rotary evaporator (rotovap), then the Pd and Au were reduced with an aqueous solution of hydrazine (no alkali hydroxide). The solid was washed to remove hydrazine, dried and potassium acetate was impregnated upon the solid. A 12.67 g(16.7 cc) charge of catalyst was placed in the reactor for testing. The results of reactor testing of this catalyst at various conditions are set forth below in Table 2. These results show an 18.2% conversion with 83% selectivity using 10.55 $O_2$, 14.31% HOAc, at 164.9° C.

EXAMPLE 2

The catalyst of this example had a composition of 1.07 wt % Pd, 0.40 wt % Au and 2.89 wt % K and was prepared according to the procedure set forth in Great Britain Patent 1,266,623 except that the support was the same as used in Example 1. A 8.68 g(11.3 cc) charge of catalyst was placed in the reactor for testing. The results of testing of this catalyst at various conditions is set forth below in Table 2 and gave 8.1% ethylene conversion and 84.4% vinyl acetate selectivity using 7% $O_2$, 10% HOAc, at 159° C.

EXAMPLE 3

The procedure of Example 2 was repeated to produce a catalyst having a composition as follows: 1.01 wt % Pd, 0.38 wt % Au and 2.60 wt % K. However, Support 1 identified above was utilized. A 9.2 g(10.6 cc) charge of catalyst was placed in the reactor for testing. The reactor testing at various conditions is set forth below in Table 2. The catalyst gave $C_2H_4$ conversion of 8.6 and VA selectivity of 85.3 under the same conditions as set forth in Example 2.

The performance of the catalyst of Examples 2 and 3 is very similar but the catalyst prepared on the Support 1 appears to be slightly more active. As the compositions of these two catalysts are nearly identical, the difference in activity may be due to the different supports.

EXAMPLE 4

This catalyst was prepared according to the teachings of U.S. Pat. No. 3,950,400 except that microspheroidal (fluid bed) Support 1 as described above was utilized. The composition was 0.82 wt % Pd, 0.40 wt % Au, 0.13 wt % Ba, 2.69 wt % K. The acetic acid was carefully removed under vacuum (using a rotary evaporator) at 60° C. This solid remained tan in color. A 11.57 g(13.4 cc) charge of catalyst was placed in the reactor for testing. Reactor testing of this catalyst set forth in Table 2 demonstrated it to be highly active and selective. At 164° C. using 7% oxygen and 14% acetic acid, 12.5% ethylene conversion was obtained with 87.2% selectivity.

EXAMPLE 5

A catalyst having the following composition: Pd 0.81 wt %, 0.34 wt % Au and 2.71 wt % K was prepared by dissolving palladium acetate (PdAc) and potassium acetate (KAc) in acetic acid, then adding gold acetate and impregnating it on Support 1. The acetic acid was removed under vacuum, at 60° C. This solid was tan in color at this point. The preparation of this catalyst is similar to that of Example 1 except there was no catalyst reduction prior to testing. A 11.75 g(13.2 cc) charge of catalyst was placed in the reactor for testing. The results of testing this catalyst under various conditions is set forth in Table 2. The catalyst gave 9.2% conversion with 87.8% VA selectivity.

EXAMPLE 6

A catalyst having the following composition: 0.77 wt % Pd, 0.40 wt % Au and 2.2 wt % K was prepared as with Example 5. The solid was then subjected to a hydrazine reduction, washed with water to remove hydrazine, and additional potassium acetate was added. A 14.25 g(17.6 cc) charge of catalyst was placed in the reactor for testing. Excellent reactor results were obtained as shown in Table 2. This catalyst gave similar results, 10.17% conversion with 85.7% selectivity, as compared with Example 5.

A variety of Pd/M/K on silica-type catalysts were prepared wherein M is not gold. Metals evaluated included M=Ba, La, Sb, Pb, Ce, Nb, Ca, Zn, and Sr. The following examples are illustrative of these various metals.

EXAMPLE 7

The catalyst was prepared with the lower level of palladium which is typically used with Bayer-type catalysts, 0.88 wt % Pd, but which is typically too inactive for use with Hoechst-type catalysts along with 0.88 wt % Ba. Acetic acid was the solvent. The catalyst had 2.9 wt % K. A 15.52 g(21.0 cc) charge of catalyst was placed in the reactor for testing. The results of testing conversions approaching 10% ethylene with 81% selectivity to VA were obtained under various conditions as set forth below in Table 2. The catalyst suffered some deactivation by exposure to an elevated temperature (100° C.) while acetic acid was still present.

EXAMPLE 8

A catalyst having 0.41 wt % Pd, 0.49 wt % Ba and 2.2 wt % K was prepared using water as the sole solvent. The mixture of palladium acetate, potassium acetate and barium acetate is sufficiently soluble in distilled water that water can be used as the sole solvent. A 24.77 g(30.0 cc) charge of catalyst was placed in the reactor for testing. Reactor testing of this catalyst under various conditions is set forth below in Table 2 and gave 10% ethylene conversion at 85% selectivity to VAM.

The use of water as the impregnating solvent instead of acetic acid has several significant advantages. Water is certainly less expensive, less toxic and less corrosive than acetic acid. All of which will give a less expensive process using water. Additionally, water does not act as a reducing agent for the palladium. When heated at 100° C. in the oven, the catalyst prepared with acetic acid darkened to near black, whereas the analogous catalyst prepared in water, retained its tan color and still retained its excellent reactor performance. Finally, water would be a more benign solvent with respect to any detrimental effects upon the support.

EXAMPLE 9

A solution of palladium acetate, potassium acetate and antimony acetate in acetic acid were impregnated upon the preformed microspheroidal support. The wet solid was dried at 60° C. under vacuum. No pre-reduction of the catalyst was performed. The resulting catalyst comprised 0.81 wt % Pd, 0.70 wt % Sb and 2.9 wt % K. A 10.95 g(12.8 cc) charge of catalyst was placed in the reactor for testing. Reactor testing shown in Table 2 gave ethylene conversions of nearly 17% with 89% selectivity at only 9 mole % oxygen in the feed mixture.

EXAMPLE 10

The addition of barium to an antimony containing catalyst substantially reduced catalyst activity. The catalyst tested had a composition (wt %) of 0.71 Pd, 0.71 Ba, 0.71 Sb and 2.6 K. A 10.95 g(13.5 cc) charge of catalyst was placed in the reactor for testing. There is no synergy between the antimony and the barium at the levels evaluated as shown by the results in Table 2 below.

EXAMPLES 11 And 12

A mixture of palladium acetate, lanthanum acetate and potassium acetate was quite soluble in acetic acid. Support 1 was used for Example 11 and Support 2A for Example 12. This solution impregnated upon the preformed support and dried under vacuum resulted in an excellent catalyst as shown in Table 2 below. The composition of catalysts 11 and 12, respectively, in weight percent were as follows: 0.77 Pd, 0.70 La, 2.7 K; 0.80 Pd, 0.57 La, 3.1 K. For Example 11, a 10.95 g(13.0 cc) charge of catalyst was placed in the reactor for testing. For Example 12, a 10.95 g(15.0 cc) charge of catalyst was placed in the reactor for testing. Conversions and selectivities were slightly lower than with the antimony-containing catalyst, but were still very good.

EXAMPLE 13

The mixture of palladium acetate, lanthanum acetate and potassium acetate was dissolved in water instead of acetic acid resulting in a catalyst having the following composition: 0.15 wt % Pd, 0.34 wt % La, 1.4 wt % K. A 25.2 g (30.0 cc) charge of catalyst was placed in the reactor for testing. Considering the low level of palladium present, the ethylene conversion of 8% as shown in Table 2 was quite good.

EXAMPLE 14

Niobium oxalate, the source of niobium utilized, was insoluble in acetic acid. For that reason the niobium oxalate was pre-impregnated onto Support 1 using an aqueous solution. After drying the support, an acetic acid solution of palladium acetate and potassium acetate was impregnated upon the support. A 11.04 g(14.0 cc) charge of catalyst was placed in the reactor for testing. Resulting catalyst composition was 0.81 wt % Pd, 0.64 wt % Nb, 3.1 wt % K. Reactor performance was adequate at ~9% conversion and 84% selectivity, but this catalyst appeared to deactivate more rapidly than expected.

EXAMPLES 15 And 16

Calcium was added as the promoter at two different levels: (1) the same mole % as barium in Example 7, and (2) at near the wt % level as barium in Example 7. In each case, Support 2A was used. For Example 15 a 10.95 g(15.8 cc) charge of catalyst was placed in the reactor for testing. For Example 16, a 10.95 g(15.4 cc) charge of catalyst was placed in the reactor for testing. Neither catalyst performed well as shown in Table 2, but the lower level of calcium gave higher conversions and higher selectivities. It is possible that adjusting the calcium level further could improve catalyst performance.

EXAMPLES 17 And 18

Cerium promoted catalyst (Example 17) and zinc promoted catalyst (Example 18) were prepared as described in the general procedure set forth above with the metals being dissolved in acetic acid and drying at 60° C. under vacuum. In each case, Support 2A was utilized. The final composition of the catalyst were: Example 17—0.80 wt % Pd, 0.69 wt % Ce, 2.8 wt % K; Example 18—0.81 wt % Pd, 0.33 wt % Zn and 2.9 wt % K. A 10.96 g(15.6 cc) charge of catalyst was placed in the reactor for testing for Example 17. For Example 18, a 10.96 g(15.6 cc) charge was used. Tests of these catalysts showed potential as shown in Table 2. Optimization of promoter level and reduction treatment could be beneficial. In particular, cerium showed very good initial activity.

EXAMPLES 19 And 20

The catalyst of Examples 19 and 20 were prepared on the same support and utilizing substantially the same procedure set forth in Examples 17 and 18 above except that Pb and Sr were substituted for Ce and Zn. The final composition of Example 19 on a wt % basis was 0.81 Pd, 0.70 Pb, 2.9 K. The final composition of Example 20 on a wt % basis was 0.80 Pd, 0.68 Sr, 2.7 K. For Example 19 a 11.71 g(13.2 cc) charge of catalyst was placed in the reactor for testing. In Example 20 a 10.95 g(15.4 cc) charge was used. As shown in Table 2, the lead promoted catalyst appeared to deactivate more rapidly than expected, while the strontium promoted catalyst was of low activity and poor selectivity.

TABLE 2

RUN DATA SUMMARY --- FLUID BED VAM IMPREGNATED CATALYSTS

| Run # | % C2H4 CONV | % VA SEL | BED T (C) | TOTAL FLOW | O2 | N2 | C2H4 | HOAC | Psig | HRS |
|---|---|---|---|---|---|---|---|---|---|---|
| Example 1 | | | | | | | | | | |
| 1 | 14.42 | 85.38 | 163.0 | 396.41 | 7.040 | 30.65 | 47.930 | 14.380 | 115 | 0.8 |
| 2 | 14.87 | 87.16 | 161.5 | 396.41 | 7.040 | 30.65 | 47.930 | 14.380 | 115 | 2.4 |
| 3 | 14.46 | 86.00 | 161.9 | 396.41 | 7.040 | 30.65 | 47.930 | 14.380 | 115 | 2.9 |
| 4 | 18.20 | 83.06 | 164.9 | 396.41 | 10.550 | 27.17 | 47.970 | 14.310 | 115 | 3.9 |
| 5 | 17.95 | 86.86 | 161.7 | 418.63 | 10.010 | 31.17 | 45.390 | 13.430 | 115 | 6.0 |
| 6 | 17.38 | 88.86 | 155.5 | 418.63 | 10.010 | 31.17 | 45.390 | 13.430 | 115 | 6.3 |
| 7 | 17.57 | 87.80 | 158.2 | 418.63 | 10.010 | 31.17 | 45.390 | 13.430 | 115 | 6.9 |
| 8 | 17.01 | 88.05 | 157.2 | 418.63 | 10.010 | 31.17 | 45.390 | 13.430 | 115 | 7.2 |
| 9 | 19.03 | 85.21 | 165.2 | 426.13 | 11.590 | 30.62 | 44.590 | 13.200 | 115 | 7.6 |
| Example 2 | | | | | | | | | | |
| 1 | 7.54 | 82.59 | 159.4 | 361.70 | 7.460 | 29.31 | 52.810 | 10.420 | 115 | 1.5 |
| 2 | 7.67 | 82.99 | 160.4 | 361.70 | 7.460 | 29.31 | 52.810 | 10.420 | 115 | 1.8 |
| 3 | 7.79 | 83.77 | 159.8 | 361.70 | 7.460 | 29.31 | 52.810 | 10.420 | 115 | 2.0 |

TABLE 2-continued

RUN DATA SUMMARY --- FLUID BED VAM IMPREGNATED CATALYSTS

| Run # | % C2H4 CONV | % VA SEL | BED T (C) | TOTAL FLOW | O2 | N2 | C2H4 | HOAC | Psig | HRS |
|---|---|---|---|---|---|---|---|---|---|---|
| 4 | 7.96 | 84.20 | 160.0 | 361.70 | 7.460 | 29.31 | 52.810 | 10.420 | 115 | 2.3 |
| 5 | 7.97 | 84.28 | 159.6 | 361.70 | 7.460 | 29.31 | 52.810 | 10.420 | 115 | 2.6 |
| 6 | 8.05 | 84.43 | 159.6 | 361.70 | 7.460 | 29.31 | 52.810 | 10.420 | 115 | 3.0 |
| 7 | 4.32 | 88.03 | 154.4 | 365.00 | 7.370 | 29.97 | 52.330 | 10.330 | 115 | 4.4 |
| 8 | 4.82 | 85.51 | 160.4 | 365.00 | 7.370 | 29.97 | 52.330 | 10.330 | 115 | 5.4 |
| 9 | 4.88 | 85.55 | 160.9 | 365.00 | 7.370 | 29.97 | 52.330 | 10.330 | 115 | 5.8 |
| 10 | 4.93 | 85.61 | 160.9 | 365.00 | 7.370 | 29.97 | 52.330 | 10.330 | 115 | 6.1 |
| 11 | 6.19 | 86.15 | 159.1 | 365.00 | 7.370 | 29.97 | 52.330 | 10.330 | 115 | 8.3 |
| 12 | 6.17 | 86.03 | 159.1 | 365.00 | 7.370 | 29.97 | 52.330 | 10.330 | 115 | 8.7 |
| 13 | 6.18 | 85.97 | 159.1 | 365.00 | 7.370 | 29.97 | 52.330 | 10.330 | 115 | 9.1 |
| 14 | 6.39 | 84.54 | 161.0 | 365.00 | 7.370 | 29.97 | 52.330 | 10.330 | 115 | 9.5 |
| 15 | 6.54 | 85.10 | 161.0 | 365.00 | 7.370 | 29.97 | 52.330 | 10.330 | 115 | 9.8 |
| 16 | 6.66 | 85.40 | 161.0 | 365.00 | 7.370 | 29.97 | 52.330 | 10.330 | 115 | 10.2 |
| Example 3 | | | | | | | | | | |
| 1 | 8.83 | 84.17 | 160.0 | 362.80 | 7.610 | 29.36 | 52.650 | 10.390 | 115 | 1.7 |
| 2 | 8.81 | 84.65 | 159.0 | 362.80 | 7.610 | 29.36 | 52.650 | 10.390 | 115 | 2.5 |
| 3 | 8.68 | 85.17 | 159.0 | 362.80 | 7.610 | 29.36 | 52.650 | 10.390 | 115 | 3.6 |
| 4 | 8.64 | 85.30 | 159.0 | 362.80 | 7.610 | 29.36 | 52.650 | 10.390 | 115 | 4.1 |
| Example 4 | | | | | | | | | | |
| 1 | 11.48 | 88.68 | 162.0 | 396.41 | 7.040 | 30.65 | 47.930 | 14.380 | 115 | 3.7 |
| 2 | 11.49 | 87.63 | 162.0 | 396.41 | 7.040 | 30.65 | 47.930 | 14.380 | 115 | 4.1 |
| 3 | 12.46 | 87.24 | 164.0 | 396.41 | 7.040 | 30.65 | 47.930 | 14.380 | 115 | 4.5 |
| 4 | 12.76 | 86.06 | 165.0 | 396.41 | 7.040 | 30.65 | 47.930 | 14.380 | 115 | 4.9 |
| Example 5 | | | | | | | | | | |
| 1 | 7.64 | 87.33 | 158.7 | 396.41 | 7.040 | 30.65 | 47.930 | 14.380 | 115 | 0.5 |
| 2 | 9.17 | 87.84 | 161.0 | 396.41 | 7.040 | 30.65 | 47.930 | 14.380 | 115 | 0.9 |
| 3 | 8.64 | 89.49 | 157.0 | 396.41 | 7.040 | 30.65 | 47.930 | 14.380 | 115 | 1.3 |
| Example 6 | | | | | | | | | | |
| 1 | 9.89 | 84.22 | 161.3 | 363.60 | 7.450 | 29.65 | 52.530 | 10.369 | 115 | 5.1 |
| 2 | 10.45 | 83.70 | 163.1 | 363.60 | 7.450 | 29.65 | 52.530 | 10.369 | 115 | 5.6 |
| 3 | 10.14 | 85.54 | 160.0 | 363.60 | 7.450 | 29.65 | 52.530 | 10.369 | 115 | 6.1 |
| 4 | 10.17 | 85.65 | 159.2 | 363.60 | 7.450 | 29.65 | 52.530 | 10.369 | 115 | 6.6 |
| 5 | 14.53 | 85.18 | 161.0 | 382.60 | 10.795 | 24.49 | 49.922 | 14.794 | 115 | 10.3 |
| 6 | 14.84 | 85.46 | 160.0 | 382.60 | 10.795 | 24.49 | 49.922 | 14.794 | 115 | 10.8 |
| 7 | 15.30 | 85.84 | 159.6 | 382.60 | 10.795 | 24.49 | 49.922 | 14.794 | 115 | 11.2 |
| 8 | 17.23 | 87.88 | 159.6 | 382.60 | 10.795 | 24.49 | 49.922 | 14.794 | 115 | 11.7 |
| 9 | 15.52 | 85.98 | 159.6 | 382.60 | 10.795 | 24.49 | 49.922 | 14.794 | 115 | 12.2 |
| Example 7 | | | | | | | | | | |
| 1 | 9.38 | 78.05 | 162.7 | 363.90 | 7.610 | 29.60 | 51.940 | 10.850 | 115 | 0.8 |
| 2 | 9.74 | 80.27 | 160.8 | 363.90 | 7.610 | 29.60 | 51.940 | 10.850 | 115 | 1.6 |
| 3 | 9.77 | 80.97 | 160.6 | 363.90 | 7.610 | 29.60 | 51.940 | 10.850 | 115 | 2.6 |
| 4 | 9.62 | 81.73 | 160.6 | 363.90 | 7.610 | 29.60 | 51.940 | 10.850 | 115 | 3.6 |
| 5 | 9.67 | 82.93 | 159.8 | 363.90 | 7.610 | 29.60 | 51.940 | 10.850 | 115 | 4.5 |
| Example 8 | | | | | | | | | | |
| 1 | 10.61 | 85.55 | 161.0 | 362.30 | 7.730 | 29.70 | 52.170 | 10.410 | 115 | 2.0 |
| 2 | 9.83 | 85.42 | 161.0 | 362.30 | 7.730 | 29.70 | 52.170 | 10.410 | 115 | 4.0 |
| Example 9 | | | | | | | | | | |
| 1 | 14.75 | 88.30 | 158.0 | 408.20 | 7.450 | 31.97 | 46.790 | 13.790 | 115 | 2.2 |
| 2 | 14.70 | 88.90 | 157.0 | 408.20 | 7.450 | 31.97 | 46.790 | 13.790 | 115 | 2.6 |
| 3 | 14.69 | 89.60 | 157.0 | 408.20 | 7.450 | 31.97 | 46.790 | 13.790 | 115 | 2.9 |
| 4 | 14.44 | 89.90 | 157.0 | 408.20 | 7.450 | 31.97 | 46.790 | 13.790 | 115 | 3.3 |
| 5 | 16.63 | 88.30 | 158.0 | 414.90 | 8.940 | 31.45 | 46.040 | 13.570 | 115 | 3.8 |
| 6 | 17.15 | 88.50 | 158.0 | 414.90 | 8.940 | 31.45 | 46.040 | 13.570 | 115 | 4.1 |
| 7 | 16.93 | 89.20 | 158.0 | 414.90 | 8.940 | 31.45 | 46.040 | 13.570 | 115 | 4.5 |
| 8 | 16.09 | 89.30 | 157.0 | 414.90 | 8.940 | 31.45 | 46.040 | 13.570 | 115 | 4.8 |
| 9 | 16.94 | 88.20 | 160.0 | 414.90 | 8.940 | 31.45 | 46.040 | 13.570 | 115 | 5.2 |
| 10 | 17.14 | 88.40 | 160.0 | 414.90 | 8.940 | 31.45 | 46.040 | 13.570 | 115 | 5.6 |
| 11 | 16.87 | 89.10 | 160.0 | 414.90 | 8.940 | 31.45 | 46.040 | 13.570 | 115 | 5.9 |
| 12 | 16.54 | 89.20 | 160.0 | 414.90 | 8.940 | 31.45 | 46.040 | 13.570 | 115 | 6.3 |
| 13 | 14.54 | 88.70 | 163.0 | 418.60 | 9.680 | 31.18 | 45.630 | 13.520 | 115 | 9.8 |
| 14 | 14.39 | 88.80 | 162.0 | 418.60 | 9.680 | 31.18 | 45.630 | 13.520 | 115 | 10.1 |
| 15 | 14.10 | 89.10 | 161.0 | 418.60 | 9.680 | 31.18 | 45.630 | 13.520 | 115 | 10.5 |
| 16 | 15.10 | 88.10 | 165.0 | 418.60 | 9.680 | 31.18 | 45.630 | 13.520 | 115 | 10.8 |
| 17 | 15.13 | 87.60 | 165.0 | 418.60 | 9.680 | 31.18 | 45.630 | 13.520 | 115 | 11.2 |
| 18 | 15.71 | 87.60 | 168.0 | 418.60 | 9.680 | 31.18 | 45.630 | 13.520 | 115 | 11.5 |
| 19 | 15.19 | 87.60 | 166.0 | 418.60 | 9.680 | 31.18 | 45.630 | 13.520 | 115 | 11.9 |

TABLE 2-continued

RUN DATA SUMMARY --- FLUID BED VAM IMPREGNATED CATALYSTS

| Run # | % C2H4 CONV | % VA SEL | BED T (C) | TOTAL FLOW | FEED COMPOSITON O2 | N2 | C2H4 | HOAC | Psig | HRS |
|---|---|---|---|---|---|---|---|---|---|---|
| Example 10 | | | | | | | | | | |
| 1 | 1.90 | 91.40 | 154.0 | 418.30 | 9.980 | 31.20 | 45.660 | 13.460 | 115 | 3.0 |
| 2 | 1.99 | 90.90 | 154.0 | 418.30 | 9.980 | 31.20 | 45.660 | 13.460 | 115 | 3.3 |
| 3 | 2.73 | 88.50 | 162.0 | 418.30 | 9.980 | 31.20 | 45.660 | 13.460 | 115 | 3.6 |
| 4 | 3.52 | 87.30 | 163.0 | 418.30 | 9.980 | 31.20 | 45.660 | 13.460 | 115 | 4.0 |
| 5 | 4.61 | 86.80 | 163.0 | 418.30 | 9.980 | 31.20 | 45.660 | 13.460 | 115 | 4.3 |
| 6 | 6.53 | 82.00 | 169.0 | 418.30 | 9.980 | 31.20 | 45.660 | 13.460 | 115 | 4.7 |
| 7 | 7.75 | 80.70 | 173.0 | 418.30 | 9.980 | 31.20 | 45.660 | 13.460 | 115 | 5.0 |
| 8 | 8.73 | 80.60 | 176.0 | 418.30 | 9.980 | 31.20 | 45.660 | 13.460 | 115 | 5.4 |
| 9 | 8.93 | 82.10 | 175.0 | 418.30 | 9.980 | 31.20 | 45.660 | 13.460 | 115 | 5.7 |
| Example 11 | | | | | | | | | | |
| 1 | 13.27 | 86.90 | 159.0 | 408.20 | 7.450 | 31.97 | 46.790 | 13.790 | 115 | 1.3 |
| 2 | 13.89 | 87.00 | 159.0 | 408.20 | 7.450 | 31.97 | 46.790 | 13.790 | 115 | 1.6 |
| 3 | 13.88 | 87.20 | 159.0 | 408.20 | 7.450 | 31.97 | 46.790 | 13.790 | 115 | 2.0 |
| 4 | 13.88 | 87.30 | 159.0 | 408.20 | 7.450 | 31.97 | 46.790 | 13.790 | 115 | 2.3 |
| 5 | 13.74 | 87.40 | 159.0 | 408.20 | 7.450 | 31.97 | 46.790 | 13.790 | 115 | 2.6 |
| 6 | 15.82 | 85.30 | 162.0 | 418.30 | 9.980 | 31.20 | 45.660 | 13.460 | 115 | 3.5 |
| 7 | 15.96 | 84.80 | 162.0 | 418.30 | 9.980 | 31.20 | 45.660 | 13.460 | 115 | 3.9 |
| 8 | 15.64 | 85.30 | 161.0 | 418.30 | 9.980 | 31.20 | 45.660 | 13.460 | 115 | 4.2 |
| 9 | 15.65 | 85.70 | 160.0 | 418.30 | 9.980 | 31.20 | 45.660 | 13.460 | 115 | 4.5 |
| 10 | 16.28 | 84.50 | 164.0 | 418.30 | 9.980 | 31.20 | 45.660 | 13.460 | 115 | 4.9 |
| 11 | 16.28 | 84.60 | 165.0 | 418.30 | 9.980 | 31.20 | 45.660 | 13.460 | 115 | 5.2 |
| 12 | 16.51 | 84.70 | 165.0 | 418.30 | 9.980 | 31.20 | 45.660 | 13.460 | 115 | 5.6 |
| 13 | 16.51 | 84.70 | 165.0 | 418.30 | 9.980 | 31.20 | 45.660 | 13.460 | 115 | 5.8 |
| Example 12 | | | | | | | | | | |
| 1 | 13.46 | 83.11 | 159.6 | 407.63 | 6.750 | 32.50 | 46.980 | 13.770 | 115 | 1.4 |
| 2 | 13.88 | 84.15 | 159.6 | 407.63 | 6.750 | 32.50 | 46.980 | 13.770 | 115 | 1.8 |
| 3 | 13.85 | 84.39 | 159.0 | 407.63 | 6.750 | 32.50 | 46.980 | 13.770 | 115 | 2.2 |
| 4 | 14.01 | 84.91 | 159.0 | 407.63 | 6.750 | 32.50 | 46.980 | 13.770 | 115 | 2.7 |
| 5 | 13.67 | 85.31 | 158.0 | 407.63 | 6.750 | 32.50 | 46.980 | 13.770 | 115 | 3.1 |
| 6 | 13.96 | 84.51 | 163.5 | 421.03 | 9.710 | 31.47 | 45.480 | 13.330 | 115 | 4.8 |
| 7 | 13.03 | 85.43 | 160.0 | 421.03 | 9.710 | 31.47 | 45.480 | 13.330 | 115 | 5.6 |
| 8 | 12.35 | 85.95 | 159.0 | 421.03 | 9.710 | 31.47 | 45.480 | 13.330 | 115 | 6.5 |
| 9 | 11.90 | 86.00 | 157.0 | 421.03 | 9.710 | 31.47 | 45.480 | 13.330 | 115 | 6.9 |
| 10 | 11.54 | 86.24 | 156.0 | 421.03 | 9.710 | 31.47 | 45.480 | 13.330 | 115 | 7.3 |
| 11 | 11.41 | 86.62 | 156.0 | 421.03 | 9.710 | 31.47 | 45.480 | 13.330 | 115 | 7.8 |
| Example 13 | | | | | | | | | | |
| 1 | 8.90 | 84.34 | 157.2 | 421.91 | 9.690 | 31.40 | 45.390 | 13.510 | 115 | 0.8 |
| 2 | 8.54 | 83.98 | 156.0 | 421.91 | 9.690 | 31.40 | 45.390 | 13.510 | 115 | 1.5 |
| 3 | 8.22 | 84.26 | 163.2 | 421.91 | 9.690 | 31.40 | 45.390 | 13.510 | 115 | 2.5 |
| 4 | 7.42 | 84.87 | 157.4 | 421.91 | 9.690 | 31.40 | 45.390 | 13.510 | 115 | 3.4 |
| 5 | 6.97 | 85.27 | 156.5 | 421.91 | 9.690 | 31.40 | 45.390 | 13.510 | 115 | 4.2 |
| Example 14 | | | | | | | | | | |
| 1 | 10.74 | 81.77 | 164.4 | 408.07 | 6.739 | 32.47 | 46.928 | 13.863 | 115 | 0.5 |
| 2 | 9.98 | 84.55 | 161.1 | 408.07 | 6.739 | 32.47 | 46.928 | 13.863 | 115 | 0.9 |
| 3 | 9.24 | 86.01 | 159.0 | 408.07 | 6.739 | 32.47 | 46.928 | 13.863 | 115 | 1.4 |
| 4 | 10.61 | 83.39 | 165.0 | 421.47 | 9.704 | 31.44 | 45.436 | 13.422 | 115 | 4.0 |
| 5 | 10.13 | 83.92 | 165.8 | 421.47 | 9.704 | 31.44 | 45.436 | 13.422 | 115 | 4.4 |
| 6 | 8.69 | 86.00 | 162.0 | 421.47 | 9.704 | 31.44 | 45.436 | 13.422 | 115 | 5.3 |
| Example 15 | | | | | | | | | | |
| 1 | 7.45 | 83.44 | 159.0 | 408.07 | 6.739 | 32.47 | 46.928 | 13.863 | 115 | 0.9 |
| 2 | 7.47 | 84.09 | 158.0 | 408.07 | 6.739 | 32.47 | 46.928 | 13.863 | 115 | 1.3 |
| 3 | 7.15 | 84.60 | 158.0 | 408.07 | 6.739 | 32.47 | 46.928 | 13.863 | 115 | 1.8 |
| 4 | 6.63 | 85.15 | 157.0 | 408.07 | 6.739 | 32.47 | 46.928 | 13.863 | 115 | 2.6 |
| 5 | 7.60 | 82.18 | 159.0 | 421.47 | 9.704 | 31.44 | 45.436 | 13.422 | 115 | 3.9 |
| 6 | 6.99 | 82.28 | 159.0 | 421.47 | 9.704 | 31.44 | 45.436 | 13.422 | 115 | 4.8 |
| 7 | 6.14 | 83.52 | 158.0 | 421.47 | 9.704 | 31.44 | 45.436 | 13.422 | 115 | 6.0 |
| Example 16 | | | | | | | | | | |
| 1 | 4.78 | 80.03 | 155.6 | 408.51 | 6.730 | 32.43 | 46.880 | 13.960 | 115 | 2.5 |
| Example 17 | | | | | | | | | | |
| 1 | 11.99 | 85.37 | 159.5 | 408.51 | 6.730 | 32.43 | 46.880 | 13.960 | 115 | 1.5 |
| 2 | 11.68 | 85.86 | 159.5 | 408.51 | 6.730 | 32.43 | 46.880 | 13.960 | 115 | 1.9 |
| 3 | 11.41 | 86.28 | 158.0 | 408.51 | 6.730 | 32.43 | 46.880 | 13.960 | 115 | 2.3 |
| 4 | 10.95 | 87.07 | 156.3 | 408.51 | 6.730 | 32.43 | 46.880 | 13.960 | 115 | 2.7 |
| 5 | 10.29 | 87.36 | 156.6 | 408.51 | 6.730 | 32.43 | 46.880 | 13.960 | 115 | 3.2 |

TABLE 2-continued

RUN DATA SUMMARY --- FLUID BED VAM IMPREGNATED CATALYSTS

| Run # | % C2H4 CONV | % VA SEL | BED T (C) | TOTAL FLOW | FEED COMPOSITON O2 | N2 | C2H4 | HOAC | Psig | HRS |
|---|---|---|---|---|---|---|---|---|---|---|
| 6 | 11.38 | 86.38 | 157.3 | 421.91 | 9.694 | 31.41 | 45.389 | 13.512 | 115 | 3.6 |
| 7 | 11.60 | 85.38 | 159.0 | 421.91 | 9.694 | 31.41 | 45.389 | 13.512 | 115 | 4.5 |
| 8 | 11.11 | 85.98 | 158.9 | 421.91 | 9.694 | 31.41 | 45.389 | 13.512 | 115 | 5.3 |
| 9 | 10.52 | 86.48 | 159.9 | 421.91 | 9.694 | 31.41 | 45.389 | 13.512 | 115 | 6.2 |
| Example 18 | | | | | | | | | | |
| 1 | 12.01 | 80.41 | 170.0 | 408.51 | 6.730 | 32.43 | 46.880 | 13.960 | 115 | 1.1 |
| 2 | 10.91 | 85.10 | 156.7 | 408.51 | 6.730 | 32.43 | 46.880 | 13.960 | 115 | 1.6 |
| 3 | 12.39 | 84.94 | 159.0 | 421.91 | 9.694 | 31.41 | 45.389 | 13.512 | 115 | 2.4 |
| 4 | 10.89 | 84.98 | 161.0 | 421.91 | 9.694 | 31.41 | 45.389 | 13.512 | 115 | 3.3 |
| 5 | 11.13 | 85.42 | 161.0 | 421.91 | 9.694 | 31.41 | 45.389 | 13.512 | 115 | 3.7 |
| 6 | 10.12 | 86.21 | 159.0 | 421.91 | 9.694 | 31.41 | 45.389 | 13.512 | 115 | 5.0 |
| 7 | 8.68 | 88.28 | 156.0 | 421.91 | 9.694 | 31.41 | 45.389 | 13.512 | 115 | 6.7 |
| 8 | 7.41 | 89.84 | 154.7 | 421.91 | 9.694 | 31.41 | 45.389 | 13.512 | 115 | 9.3 |
| Example 19 | | | | | | | | | | |
| 1 | 10.66 | 84.76 | 162.9 | 408.51 | 6.730 | 32.43 | 46.880 | 13.960 | 115 | 1.4 |
| 2 | 9.34 | 85.79 | 158.5 | 408.51 | 6.730 | 32.43 | 46.880 | 13.960 | 115 | 2.3 |
| 3 | 8.82 | 86.11 | 158.5 | 421.91 | 9.694 | 31.41 | 45.389 | 13.512 | 115 | 3.1 |
| 4 | 7.34 | 87.94 | 158.5 | 421.91 | 9.694 | 31.41 | 45.389 | 13.512 | 115 | 4.4 |
| Example 20 | | | | | | | | | | |
| 1 | 6.06 | 82.27 | 156.8 | 408.51 | 6.730 | 32.43 | 46.880 | 13.960 | 115 | 1.4 |
| 2 | 5.66 | 83.00 | 156.8 | 408.51 | 6.730 | 32.43 | 46.880 | 13.960 | 115 | 3.1 |
| 3 | 5.11 | 83.60 | 156.8 | 408.51 | 6.730 | 32.43 | 46.880 | 13.960 | 115 | 6.1 |

REACTOR TESTING FOR EXAMPLES 21 TO 35

The catalysts were tested in a bench scale fluid bed reactor with a maximum catalyst capacity of 40 cm$^3$. 30 cm$^3$ of catalyst or catalyst-plus-diluent was the volume of solid loaded into the reactor for each experiment. For some of the experiments, the total of 30 cm$^3$ reactor volume was obtained by mixing sufficient microspheroidal silica diluent (loaded with Au and KOAc only) with the active catalyst prior to reactor testing. The reactor was equipped with two feed inlets. For some of the experiments of this study, ethylene, acetic acid, and oxygen all entered the reactor through the lower inlet and nitrogen only was fed through the central inlet. In other tests, additional oxygen was fed through the central feed inlet. This central inlet was located 2.5 inches above the lower feed inlet.

The reactor pressure was controlled at 115 psig and all lines leading to and from the reactor were heat traced and maintained at 150° to 160° C. in order to prevent condensation of liquid feeds or products. Typical temperatures for the fluid bed reactor can vary between 100° to 250° C., preferably 135° to 190° C.

The gaseous reactor effluent was analysed on-line using a Hewlett Packard Model 5890 gas chromatograph equipped with both TCD and FID detectors. Oxygen, nitrogen, ethylene and carbon dioxide were separated on a 13× mole sieve column parallel with 10% Carbowax 20M on 80/100 Chromosorb WAW and 23% SP2700 on 80/100 Chromosorb PAW, and quantified with the TCD. Vinyl acetate and acetic acid and other organic by-products were separated on a J&W DB1701 megabore capillary column and quantified with the FID. Data was analyzed via a customized Excel spreadsheet.

Support Preparation

The support used for all catalyst preparations was prepared by spray drying a mixture of Nalco (Nalco Chemical Co) silica sol 1060 and DeGussa Aerosil® (DeGussa Chemical Company) silica. In the dried support, 80% of the silica came from the sol and 20% of the silica came from a silica source such as Aerosil®. The spray dried microspheres were calcined in air at 640° C. for 4 hours. It should be understood that the support preparation given above is not intended to be restricted to this type of silica sol or to this particular silica.

Prior to use, the support was sieved to remove particles of diameter greater than 105 microns. The particle size distribution of the resulting support was used in all catalyst preparations:

| Particle Size | % |
|---|---|
| 90–105 microns | 18.5 |
| 45–90 microns | 56.1 |
| <45 microns | 25.4 |

It should be understood that the particle size distribution recited above is not intended to be limiting and that variations in this distribution are contemplated depending upon reactor size and operating conditions.

Catalyst Preparation

The following procedures describe the method of preparation of a fluid bed vinyl acetate catalyst with a metals loading of 0.42 wt % Pd, 0.21 wt % Au and 7.0 wt % KOAc. Catalysts with different Pd and Au loadings were prepared by simply scaling the amounts of Na$_2$PdCl$_4$.xH$_2$O and HAuCl$_4$.xH$_2$O used in the preparation. (It should be noted that alternative water-soluble sources of Pd and Au could be used in place of Na$_2$PdCl$_4$.xH$_2$O and HAuCl$_4$.xH$_2$O.)

Catalyst Preparation—Standard Procedure A
Stage 1 Pd, Au Impregnation (non-sequential)

30.0 g of microspheroidal silica support was impregnated with a solution of Na$_2$PdCl$_4$.xH$_2$O (0.4747 g, 28.9% Pd) and HAuCl$_4$.xH$_2$O (0.1370 g, 49.0% Au) in distilled H$_2$O (30.0 cm$^3$) by incipient wetness. The resulting mixture was mixed thoroughly and then left to stand for 1 hour. After this time the mixture was dried overnight at 60° C.

Stage 2 Reduction and Washing

The impregnated, dried silica (from stage 1) was allowed to cool to room temperature, and then a solution of hydrazine (3.0 g of a 55% aqueous solution of N$_2$H$_4$) in 80.0 cm$^3$ distilled H$_2$O was added slowly, and the mixture allowed to stand for 3 hours with occasional stirring. After this time, the mixture was filtered and washed with 4×250 cm$^3$ distilled H$_2$O, and then air-dried at room temperature. The solid was then dried overnight at 60° C.

Stage 3 KOAc Treatment The treated silica (from stage 2) was then impregnated with a solution of KOAc in distilled H$_2$O (30.0 cm$^3$) by incipient wetness. The amount of KOAc used was sufficient to give a final loading of 7 wt % KOAc on the silica (ie 2.258 g KOAc required for 30 g treated silica). The resulting mixture was mixed thoroughly and then left to stand for 1 hour. After this time the mixture was dried overnight at 60° C.

Catalyst Preparation—Standard Procedure B
Stage 1 Pd, Au Impregnation (sequential)

30.0 g of microspheroidal silica support was impregnated with a solution of Na$_2$PdCl$_4$.xH$_2$O (0.4747 g, 28.9% Pd) in distilled H$_2$O (30.0 cm$^3$) by incipient wetness. The resulting mixture was mixed thoroughly and then left to stand for 1 hour. After this time the mixture was dried overnight at 60° C. The impregnated, dried silica was then impregnated with a solution of HAuCl$_4$.xH$_2$O (0.1370 g, 49.0% Au) by incipient wetness. The resulting mixture was mixed thoroughly and then left to stand for 1 hour. After this time the mixture was dried overnight 60° C.

Stages 2 and 3
As for Standard Procedure A.

EXAMPLES 21 TO 35

Catalysts prepared by the above method were tested for the acetoxylation of ethylene and the results are collated in Tables 3 to 5. For Examples 21 to 29 (Tables 3 and 4), oxygen conversion was maintained at a constant level (approx. 30% ) and Au/K loaded diluent was used with the active catalyst; this enabled catalysts of high activity to be tested. Examples 21 to 25 (Table 3) demonstrate that as metals loadings are increased, catalyst activity increases. For Examples 21 to 25, the Au/Pd ratio is a constant (Au/Pd =0.5).

Examples 26 to 28 (Table 4) show the effect of use of a higher Au/Pd ratio (Au/Pd=2.0). Activity per g of Pd is higher for these catalysts compared to those at the lower Au/Pd ratio. Selectivity to VA is also higher at the higher Au/Pd ratio.

Example 29 (Table 4) demonstrates that the Au/K diluent is inert.

For Examples 30 to 35 (Table 5), the reactor was filled with catalyst (i.e. no diluent was used), and oxygen conversion was allowed to vary. The purpose of these examples is to demonstrate high ethylene conversion. Au/Pd ratios of 0.5, 1.0, 1.3, 1.9 and 2.0 were employed. Example 35, where the Au/Pd ratio is 1.9, shows both high ethylene conversion (up to 19.4% ) and high selectivity (up to 90.8%).

TABLE 3

| Example[a] | Run # | Wt % Pd[b] | Wt % Au[b] | Wt. of Cat./g | Wt. of Pd[b]/g | Bed temp. | Bath temp. | % O$_2$ Conv. | % C$_2$H$_4$ Conv. | % VA Selectivity | g VA/ g Pd/h | g VA/ kg-cat/h | Time on stream/h |
|---|---|---|---|---|---|---|---|---|---|---|---|---|---|
| 21 | 17551-21 | 0.42 | 0.21 | 7.00 | 0.0296 | 152 | 148 | 32.9 | 6.2 | 85.8 | 70.6 | 299 | 0.5 |
|  |  |  |  |  |  | 152 | 147 | 32.0 | 6.3 | 86.1 | 72.5 | 306 | 1.5 |
|  |  |  |  |  |  | 152 | 147 | 32.0 | 6.2 | 87.5 | 72.6 | 308 | 2.5 |
|  |  |  |  |  |  | 153 | 147 | 32.8 | 6.9 | 85.5 | 79.3 | 335 | 3.5 |
|  |  |  |  |  |  | 153 | 147 | 33.5 | 6.9 | 87.9 | 81.3 | 344 | 4.3 |
| 22 | 17551-66[c] | 0.64 | 0.31 | 5.10 | 0.0324 | 153 | 147 | 32.3 | 7.3 | 88.7 | 78.4 | 498 | 0.7 |
|  |  |  |  |  |  | 153 | 147 | 32.7 | 7.5 | 89.1 | 81.5 | 518 | 1.5 |
|  |  |  |  |  |  | 152 | 146 | 33.5 | 7.7 | 88.4 | 83.1 | 529 | 2.5 |
|  |  |  |  |  |  | 153 | 146 | 34.6 | 7.9 | 89.0 | 85.6 | 545 | 3.5 |
|  |  |  |  |  |  | 152 | 146 | 34.4 | 8.0 | 89.8 | 87.6 | 558 | 4.3 |
| 23 | 17551-27 | 0.85 | 0.42 | 3.40 | 0.0288 | 153 | 148 | 29.1 | 6.5 | 88.1 | 78.4 | 663 | 0.5 |
|  |  |  |  |  |  | 152 | 147 | 28.9 | 7.0 | 87.0 | 82.5 | 698 | 1.5 |
|  |  |  |  |  |  | 152 | 147 | 31.6 | 7.1 | 88.4 | 86.1 | 729 | 2.5 |
|  |  |  |  |  |  | 152 | 147 | 30.9 | 7.4 | 87.0 | 87.3 | 738 | 3.5 |
|  |  |  |  |  |  | 152 | 147 | 32.1 | 7.3 | 89.0 | 88.5 | 749 | 4.3 |
| 24 | 17551-62 | 1.05 | 0.52 | 2.95 | 0.0312 | 153 | 147 | 33.5 | 7.4 | 88.9 | 82.8 | 876 | 0.7 |
|  |  |  |  |  |  | 153 | 147 | 34.4 | 7.8 | 87.8 | 86.3 | 914 | 1.7 |
|  |  |  |  |  |  | 152 | 146 | 34.6 | 7.9 | 90.0 | 89.5 | 948 | 2.5 |
|  |  |  |  |  |  | 152 | 146 | 35.2 | 8.0 | 89.6 | 90.0 | 953 | 3.5 |
|  |  |  |  |  |  | 152 | 146 | 34.7 | 7.9 | 90.2 | 89.5 | 948 | 4.3 |
| 25 | 17551-32 | 1.27 | 0.62 | 2.26 | 0.0287 | 152 | 150 | 16.7 | 3.7 | 83.1 | 42.1 | 534 | 0.5 |
|  |  |  |  |  |  | 153 | 149 | 22.8 | 4.9 | 85.7 | 57.7 | 733 | 1.5 |
|  |  |  |  |  |  | 152 | 148 | 26.0 | 5.6 | 85.9 | 65.5 | 831 | 2.5 |
|  |  |  |  |  |  | 153 | 148 | 28.2 | 5.9 | 83.9 | 67.7 | 859 | 3.5 |
|  |  |  |  |  |  | 152 | 147 | 28.4 | 5.8 | 87.3 | 69.4 | 880 | 4.5 |

[a]For all experiments: Inlet composition equals 7.6% O$_2$, 10% AcOH, 53% C$_2$H$_4$ (all volume %), balance N$_2$. All reactant gases fed through inlet at base of reactor. Au/K diluent used to make up combined catalyst plus diluent volume to 30 cm$^3$.
[b]These values are calculated based on the quantity of metal salt used in catalyst preparation.
[c]Indicates sequential impregnation of Pd and then Au was employed in catalyst preparation.

TABLE 4

| Example[a] | Run # | Wt % Pd[b] | Wt % Au[b] | Wt. of Cat./g | Wt. of Pd[b]/g | Bed temp. | Bath temp. | % O$_2$ Conv. | % C$_2$H$_4$ Conv. | % VA Selectivity | g VA/ g Pd/h | g VA/ kg-cat/h | Time on stream/h |
|---|---|---|---|---|---|---|---|---|---|---|---|---|---|
| 26 | 17551-41[c] | 0.42 | 0.83 | 5.45 | 0.0231 | 152 | 150 | 24.0 | 5.9 | 88.6 | 88.8 | 376 | 0.5 |
|  |  |  |  |  |  | 153 | 149 | 27.5 | 7.0 | 90.8 | 107.7 | 456 | 1.5 |
|  |  |  |  |  |  | 152 | 148 | 29.2 | 7.3 | 90.3 | 112.2 | 475 | 2.5 |
|  |  |  |  |  |  | 153 | 148 | 31.2 | 7.6 | 92.3 | 119.9 | 508 | 3.5 |
|  |  |  |  |  |  | 153 | 148 | 31.6 | 7.9 | 91.6 | 122.9 | 521 | 4.3 |
| 27 | 17551-57 | 0.64 | 1.25 | 4.27 | 0.0272 | 153 | 147 | 31.8 | 7.3 | 90.0 | 96.5 | 614 | 0.5 |
|  |  |  |  |  |  | 153 | 147 | 32.5 | 7.7 | 91.2 | 102.7 | 653 | 1.5 |
|  |  |  |  |  |  | 153 | 146 | 32.8 | 7.8 | 91.9 | 105.0 | 668 | 2.5 |
|  |  |  |  |  |  | 152 | 146 | 33.0 | 7.8 | 90.8 | 103.3 | 657 | 3.5 |
|  |  |  |  |  |  | 152 | 146 | 33.3 | 8.0 | 91.0 | 107.0 | 681 | 4.3 |
| 28 | 17551-53 | 0.85 | 1.66 | 3.77 | 0.0319 | 152 | 146 | 34.0 | 7.9 | 90.2 | 89.5 | 758 | 0.5 |
|  |  |  |  |  |  | 153 | 146 | 35.8 | 8.3 | 92.0 | 95.3 | 807 | 1.5 |
|  |  |  |  |  |  | 153 | 146 | 37.6 | 9.2 | 89.7 | 103.2 | 875 | 2.5 |
|  |  |  |  |  |  | 153 | 145 | 36.3 | 8.8 | 91.2 | 100.2 | 849 | 3.5 |
|  |  |  |  |  |  | 152 | 145 | 33.3 | 8.7 | 91.1 | 99.4 | 842 | 4.3 |
| 29 | 17551-71 | 0 | 0 | 0 | 0 (diluent only) | 151 | 150 | 1.1 | 0.5 | — | — | — | 0.5 |
|  |  |  |  |  |  | 150 | 149 | -0.8 | 0.5 | — | — | — | 1.5 |
|  |  |  |  |  |  | 150 | 150 | -0.1 | 0.6 | — | — | — | 2.5 |
|  |  |  |  |  |  | 150 | 149 | 0.7 | 0.6 | — | — | — | 3.5 |

[a]For all experiments: Inlet composition equals 7.6% O$_2$, 10% AcOH, 53% C$_2$H$_4$ (all volume %), balance N$_2$. All reactant gases fed through inlet at base of reactor. Au/K diluent used to make up combined catalyst plus diluent volume to 30 cm$^3$.
[b]These values are calculated based on the quantity of metal salt used in catalyst preparation.
[c]Indicates sequential impregnation of Pd and then Au was employed in catalyst preparation.

TABLE 5

| Example[a] | Run # | Wt % Pd[b] | Wt % Au[b] | Wt. of Cat./g | Wt. of Pd[b]/g | Bed temp. | Bath temp. | % O$_2$ fed | % AcOH fed | % O$_2$ Conv. | % C$_2$H$_4$ Conv. | % VA Selectivity | g VA/ g Pd/h | g VA/ kg-cat/h | Time on stream/h |
|---|---|---|---|---|---|---|---|---|---|---|---|---|---|---|---|
| 30 | 17513-61[c] | 0.22 | 0.11 | 21.91 | 0.0464 | 154 | 150 | 7.6 | 10.1 | 21.3 | 5.1 | 84.3 | 36.1 | 77 | 0.5 |
|  |  |  |  |  |  | 156 | 150 | 7.6 | 10.1 | 26.0 | 6.0 | 83.4 | 42.3 | 90 | 1.5 |
|  |  |  |  |  |  | 154 | 147 | 7.6 | 10.1 | 27.0 | 6.2 | 86.5 | 45.3 | 96 | 2.7 |
|  |  |  |  |  |  | 158 | 149 | 7.6 | 10.1 | 32.5 | 6.9 | 85.0 | 49.6 | 105 | 3.6 |
|  |  |  |  |  |  | 159 | 150 | 7.6 | 10.1 | 36.3 | 7.4 | 85.1 | 53.5 | 113 | 4.5 |
| 31 | 17513-40[c] | 0.42 | 0.21 | 22.03 | 0.0932 | 152 | 138 | 7.6 | 10.1 | 65.0 | 12.5 | 87.3 | 46.5 | 197 | 0.5 |
|  |  |  |  |  |  | 153 | 138 | 9.1 | 11.9 | 57.4 | 13.1 | 87.2 | 48.3 | 204 | 1.5 |
|  |  |  |  |  |  | 155 | 140 | 9.1 | 11.9 | 57.7 | 14.5 | 87.8 | 54.0 | 229 | 3.2 |
|  |  |  |  |  |  | 159 | 141 | 10.5 | 14.1 | 58.2 | 15.6 | 86.4 | 57.1 | 242 | 4.2 |
|  |  |  |  |  |  | 162 | 143 | 10.5 | 14.1 | 58.6 | 16.0 | 85.4 | 57.8 | 245 | 4.9 |
| 32 | 17513-14[c] | 0.42 | 0.43 | 21.87 | 0.0926 | 154 | 135 | 7.6 | 10.2 | 81.0 | 14.7 | 87.8 | 54.5 | 231 | 0.5 |
|  |  |  |  |  |  | 155 | 135 | 9.1 | 12.2 | 73.5 | 16.4 | 87.2 | 60.3 | 256 | 1.5 |
|  |  |  |  |  |  | 153 | 135 | 10.4 | 14.5 | 67.2 | 16.8 | 87.4 | 61.9 | 262 | 2.5 |
|  |  |  |  |  |  | 157 | 138 | 10.4 | 14.5 | 68.8 | 16.6 | 84.4 | 58.8 | 249 | 3.5 |
|  |  |  |  |  |  | 162 | 140 | 10.4 | 14.5 | 80.2 | 17.2 | 83.1 | 60.1 | 255 | 4.4 |
| 33 | 17513-56[c] | 0.32 | 0.43 | 21.87 | 0.0695 | 154 | 138 | 7.6 | 10.2 | 75.7 | 15.1 | 89.2 | 76.5 | 243 | 0.5 |
|  |  |  |  |  |  | 154 | 138 | 9.1 | 12.3 | 65.9 | 16.0 | 89.5 | 81.8 | 260 | 1.5 |
|  |  |  |  |  |  | 155 | 138 | 10.5 | 14.2 | 61.3 | 17.2 | 88.0 | 86.3 | 274 | 2.5 |
|  |  |  |  |  |  | 157 | 139 | 10.5 | 14.2 | 65.6 | 17.3 | 88.2 | 86.9 | 276 | 3.5 |
| 34 | 17513-29[c] | 0.22 | 0.43 | 21.88 | 0.0463 | 153 | 144 | 7.6 | 10.0 | 64.5 | 12.8 | 90.2 | 99.0 | 210 | 0.5 |
|  |  |  |  |  |  | 154 | 144 | 9.1 | 12.2 | 55.8 | 13.8 | 90.1 | 106.3 | 225 | 1.5 |
|  |  |  |  |  |  | 157 | 146 | 9.1 | 12.2 | 61.1 | 14.5 | 89.5 | 110.9 | 235 | 2.5 |
|  |  |  |  |  |  | 158 | 147 | 10.5 | 14.0 | 55.2 | 14.4 | 88.8 | 109.3 | 231 | 3.5 |
|  |  |  |  |  |  | 161 | 149 | 10.5 | 14.0 | 59.5 | 15.5 | 87.9 | 116.7 | 247 | 4.4 |
| 35 | 17551-03[c] | 0.32 | 0.62 | 21.87 | 0.0692 | 153 | 136 | 7.6 | 10.2 | 72.7 | 14.7 | 90.0 | 74.9 | 238 | 0.5 |
|  |  |  |  |  |  | 153 | 137 | 9.1 | 12.2 | 65.4 | 16.3 | 89.2 | 82.4 | 261 | 1.5 |
|  |  |  |  |  |  | 154 | 137 | 10.5 | 14.2 | 61.2 | 19.4 | 90.8 | 100.0 | 318 | 2.7 |
|  |  |  |  |  |  | 152 | 137 | 10.5 | 14.2 | 58.2 | 16.8 | 89.7 | 85.6 | 272 | 3.5 |
|  |  |  |  |  |  | 156 | 139 | 10.5 | 14.2 | 51.4 | 17.7 | 88.8 | 89.1 | 283 | 4.3 |

[a]For all experiments: Inlet composition of O$_2$ and AcOH as stated in Table, 53% C$_2$H$_4$ (all volume %), balance N$_2$. AcOH, C$_2$H$_4$ and 7.6% O$_2$ fed through inlet at base of reactor. Additional O$_2$ fed through second inlet to reactor.
[b]These values are calculated based on the quantity of metal salt used in catalyst preparation.
[c]Indicates sequential impregnation of Pd and then Au was employed in catalyst preparation.

What we claim as our invention is:

1. A process to manufacture vinyl acetate monomer comprising contacting ethylene, acetic acid, and an oxygen-containing gas in a fluidized bed reactor under fluidized bed reaction conditions with a fluid bed vinyl acetate monomer catalyst comprising a preformed fluidizable microspheroidal inert catalyst support having a pore volume of 0.2 to 0.7 cc/gram with at least 50% of microspheroidal catalyst support particles having a diameter of less than 105 microns; palladium metal; a metal, M, selected from the group consisting of barium, gold, lanthanum, niobium, cerium, zinc, lead, calcium, strontium, antimony, and mixtures thereof; and at least one alkali metal.

2. The process to manufacture vinyl acetate monomer of claim 1 wherein the reaction temperature is 100 to 250° C.

3. The process to manufacture vinyl acetate monomer of claim 1 wherein the fluid bed vinyl acetate monomer catalyst contains 0.2 to 4 wt. % palladium, 0.1 to 5 wt. % alkali metal, and 0.1 to 4 wt. % gold.

4. The process to manufacture vinyl acetate monomer of claim 1 wherein the fluid bed vinyl acetate monomer catalyst is prepared by impregnating the preformed catalyst support with salts of palladium and M metals followed by reduction.

5. The process to manufacture vinyl acetate monomer of claim 1 wherein the fluid bed vinyl acetate monomer catalyst contains at least 75% microspheroidal particles having a diameter of less than 105 microns.

6. The process to manufacture vinyl acetate monomer of claim 1 wherein M in the fluid bed vinyl acetate monomer catalyst is barium, gold, lanthanum, niobium, cerium, zinc, lead, calcium, strontium, and mixtures thereof.

7. The process to manufacture vinyl acetate monomer of claim 1 wherein the preformed microspheroidal support, in the fluid bed vinyl acetate monomer catalyst, comprise silica.

8. The process to manufacture vinyl acetate monomer of claim 1 wherein the preformed inert catalyst support is formed by:
  (a) preparing an aqueous mixture of a silica sol and solid substantially inert silica particles;
  (b) spray drying the mixture to form microspheroidal particles; and
  (c) calcining the spray-dried microspheroidal particles.

9. The process to manufacture vinyl acetate monomer of claim 8 wherein M in the fluid bed vinyl acetate monomer catalyst is gold.

10. The process to manufacture vinyl acetate monomer of claim 8 wherein the dried and calcined microspheroidal particles in the fluid bed vinyl acetate monomer catalyst have a pore volume of 0.3 to 0.65 cc/gram.

11. The process to manufacture vinyl acetate monomer of claim 8 wherein the preformed catalyst support in the fluid bed vinyl acetate monomer catalyst is formed from a mixture of a silica sol and solid substantially inert silica particles in which the silica sol has a particle size of about 40–80 nanometers.

12. The process to manufacture vinyl acetate monomer of claim 8 wherein the preformed catalyst support in the fluid bed vinyl acetate monomer catalyst is formed from a mixture of a silica sol and solid substantially inert silica particles in which more than about 20 wt. % of the silica is from the sol.

13. The process to manufacture vinyl acetate monomer of claim 8 wherein the preformed catalyst support in the fluid bed vinyl acetate monomer catalyst is formed from a mixture of a silica sol and solid substantially inert silica particles in which more than about 35 wt. % of the silica is from the sol.

14. The process to manufacture vinyl acetate monomer of claim 8 wherein the dried and calcined microspheroidal particles in the fluid bed vinyl acetate monomer catalyst have a surface area of 120 to 190 m²/gram.

15. A process to manufacture vinyl acetate monomer comprising contacting ethylene, acetic acid, and an oxygen-containing gas in a fluidized bed reactor under fluidized bed reaction conditions with a fluid bed vinyl acetate monomer catalyst produced by
  A. impregnating a pre-formed inert catalyst support made by:
    (a) preparing an aqueous mixture of a silica sol and solid substantially inert silica particles;
    (b) spray drying the mixture to form microspheroidal particles; and
    (c) calcining the spray-dried microspheroidal particles to form a fluidizable microspheroidal catalyst support having a pore volume of 0.2 to 0.7 cc/gram with at least 50% of the microspheroidal particles having a diameter of less than 105 microns;
    with aqueous halide-free salts of palladium; and a metal, M, selected from the group consisting of barium, gold, lanthanum, niobium, cerium, zinc, lead, calcium, strontium, antimony, and mixtures thereof;
  B. impregnating the catalyst support with at least one alkali metal salt;
  C. reducing the palladium and M metals before or after alkali metal salt impregnation; and
  D. drying the impregnated support;
  to form fluidizable vinyl acetate monomer catalyst.

16. The process to manufacture vinyl acetate monomer of claim 15 wherein the aqueous mixture of a silica sol and a solid substantially inert silica particles used to produce the pre-formed inert catalyst support in the fluid bed vinyl acetate monomer catalyst is substantially free of organic solvent.

17. The process to manufacture vinyl acetate monomer of claim 15 wherein the preformed catalyst support in the fluid bed vinyl acetate monomer catalyst is formed from a mixture of a silica sol and a solid substantially inert silica particles in which the solid substantially inert silica particles have little or no micropores, and have a mesopore volume of about 1.5 to 0.25 cc/g and a surface area of 80 to 200 m²/g.

18. The process to manufacture vinyl acetate monomer of claim 15 wherein M in the fluid bed vinyl acetate monomer catalyst is barium, gold, lanthanum, niobium, cerium, zinc, lead, calcium, strontium, and mixtures thereof.

19. The process to manufacture vinyl acetate monomer of claim 15 wherein the preformed catalyst support in the fluid bed vinyl acetate monomer catalyst contains at least 75% microspheroidal particles having a diameter of less than 105 microns.

20. The process to manufacture vinyl acetate monomer of claim 15 wherein the solid substantially inert particles used in the preparation of the microspheroidal particles are fumed silica.

21. A process to manufacture vinyl acetate monomer comprising contacting ethylene, acetic acid, and an oxygen-containing gas in a fluidized bed reactor under fluidized bed reaction conditions with a fluid bed vinyl acetate monomer catalyst produced by:
  A. impregnating a pre-formed inert catalyst support made by
    (a) preparing an aqueous mixture of a silica sol and solid substantially inert silica particles;
    (b) spray drying the mixture to form microspheroidal particles; and
    (c) calcining the spray-dried microspheroidal particles to form a fluidizable microspheroidal catalyst support having a pore volume of 0.2 to 0.7 cc/gram with at least 50% of the microspheroidal particles having a diameter of less than 105 microns;
    with aqueous chloride salts of palladium; and aqueous chloride salts of a metal, M, selected from the group consisting of barium, gold, lanthanum, niobium, cerium, zinc, lead, calcium, strontium, antimony, and mixtures thereof;

B. impregnating the catalyst support with at least one alkali metal salt;

C. reducing the palladium and M metals before or after alkali metal salt impregnation; and D. drying the impregnated support; to form a fluidizable vinyl acetate monomer catalyst.

22. The process to manufacture vinyl acetate monomer of claim 21 wherein M in the fluid bed vinyl acetate monomer catalyst is barium, gold, lanthanum, niobium, cerium, zinc, lead, calcium, strontium, and mixtures thereof.

23. The process to manufacture vinyl acetate monomer of claim 21 wherein the preformed catalyst support in the fluid bed vinyl acetate monomer catalyst contains at least 75% microspheroidal particles having a diameter of less than 105 microns.

24. The process to manufacture vinyl acetate monomer of claim 21 wherein the preformed catalyst support in the fluid bed vinyl acetate monomer catalyst has a bulk density of 0.6 to 0.8 g/cc.

25. The process to manufacture vinyl acetate monomer of claim 21 wherein the preformed catalyst support in the fluid bed vinyl acetate monomer catalyst has a surface area of 50 to 200 $m^2/g$.

26. The process of claim 15 wherein the alkali metal salt is impregnated onto the catalyst support after reduction of the palladium and M metals.

27. The process of claim 21 wherein the alkali metal salt is impregnated onto the catalyst support after reduction of the palladium and M metals.

* * * * *

UNITED STATES PATENT AND TRADEMARK OFFICE
CERTIFICATE OF CORRECTION

PATENT NO. : 6,399,813 B1
DATED : June 4, 2002
INVENTOR(S) : Patricia Rae Blum et al.

It is certified that error appears in the above-identified patent and that said Letters Patent is hereby corrected as shown below:

Column 3,
Line 17, "microns. 76" should read -- microns. --

Column 4,
Lines 15 and 16, "temperatures for the ago fluid" should read -- temperatures for the fluid --

Column 9,
Line 45, "adequate at -9% conversion" should read -- adequate at ~9% conversion --

Signed and Sealed this

Twentieth Day of July, 2004

JON W. DUDAS
*Acting Director of the United States Patent and Trademark Office*